(12) United States Patent
McHugh et al.

(10) Patent No.: US 9,938,682 B2
(45) Date of Patent: Apr. 10, 2018

(54) LONG-EXPOSURE, TIME-INTEGRATED SAMPLER FOR GROUNDWATER OR THE LIKE

(71) Applicant: GSI ENVIRONMENTAL, INC., Houston, TX (US)

(72) Inventors: Thomas E. McHugh, Houston, TX (US); Lisa J. Molofsky, Houston, TX (US); David T. Adamson, Houston, TX (US); Charles J. Newell, Houston, TX (US)

(73) Assignee: GSI Environmental, Inc., Houston, TX (US)

( * ) Notice: Subject to any disclaimer, the term of this patent is extended or adjusted under 35 U.S.C. 154(b) by 155 days.

(21) Appl. No.: 15/157,013

(22) Filed: May 17, 2016

(65) Prior Publication Data

US 2016/0341705 A1 Nov. 24, 2016

Related U.S. Application Data

(60) Provisional application No. 62/164,321, filed on May 20, 2015.

(51) Int. Cl.
| | |
|---|---|
| *E02D 1/06* | (2006.01) |
| *G01N 1/10* | (2006.01) |
| *G01N 1/12* | (2006.01) |
| *G01N 1/22* | (2006.01) |
| *G01N 30/00* | (2006.01) |

(52) U.S. Cl.
CPC ............... *E02D 1/06* (2013.01); *G01N 1/10* (2013.01); *G01N 1/12* (2013.01); *G01N 1/2214* (2013.01); *G01N 2001/1012* (2013.01); *G01N 2030/009* (2013.01)

(58) Field of Classification Search
None
See application file for complete search history.

(56) References Cited

U.S. PATENT DOCUMENTS

| | | | | |
|---|---|---|---|---|
| 6,050,150 A | * | 4/2000 | Underhill | G01N 1/2273 210/690 |
| 2014/0069184 A1 | * | 3/2014 | McAlary | E21B 49/081 73/152.28 |

\* cited by examiner

*Primary Examiner* — Manish S Shah
*Assistant Examiner* — Jean Morello
(74) *Attorney, Agent, or Firm* — Blank Rome LLP (57) ABSTRACT

A system, device, and method quantitatively measure average concentrations of target constituents (e.g., volatile organic compounds (VOCs)) in an ambient fluid (e.g., groundwater, surface water, air, etc.) over an extended period of time. The system uses a passive device having an outer equilibration chamber and an inner kinetic sampler. The device is placed in an ambient fluid for a specified period of time, wherein the target constituent(s) rapidly diffuse through a high-permeability membrane into the fluid-filled equilibration chamber. From there, the target constituents are taken up by an uptake rate the kinetic sampler that is configured to be less than an equilibration rate of the equilibration chamber.

29 Claims, 4 Drawing Sheets

LONG-EXPOSURE, TIME-INTEGRATED SAMPLER FOR GROUNDWATER OR THE LIKE

CROSS-REFERENCE TO RELATED APPLICATIONS

This application claims the benefit of U.S. Provisional Appl. 62/164,321, filed 20 May 2015, which is incorporated herein by reference in its entirety.

BACKGROUND OF THE DISCLOSURE

The most common method of measuring the concentration of contaminants and other constituents in environmental media, such as water and air, involves collecting "grab samples" (i.e., the direct collection of a sample of the environmental media over a time period of minutes or less, such that it represents the concentration at an instant in time). Most of the currently available sampling methods (e.g., purge sampling; SNAP Sampler as in U.S. Pat. No. 7,178,415, HYDRASleeve as in U.S. Pat. Nos. 6,481,300 & 6,837,120; etc.) collect such grab samples.

However, grab samples can be significantly affected by short-term variability in the concentrations of contaminants in the environment. Short-term variability has been shown to primarily occur over a time scale of days to weeks or less, and can present as a seemingly random increase or decrease in contaminant concentrations unrelated to the long-term trends associated with ongoing impacts, natural contaminant attenuation, or site remediation. Because grab samples capture the concentration at an instant in time, rather than a period of time, the grab samples are particularly subject to the effects of short-term variability, making it difficult to observe meaningful trends in concentration over time.

As a result of the random variability associated with grab samples (i.e., individual grab samples commonly over-estimate or under-estimate the average concentration by a factor of 2×, and sometimes by as much as 10×), additional sample locations and more frequent sampling events are often utilized to better understand the overall trend in concentrations. However, increased monitoring can drive up costs, and may still yield incorrect conclusions. For example, even in a network of 10 or 20 monitoring wells used for measuring groundwater pollution, concerns may be raised after only one of the monitoring wells in the network shows increasing concentrations in one sampling event despite the fact that the likely explanation for this apparent increase in concentration is natural short-term variability.

To address these problems, the environmental monitoring field is moving away from these types of methods of obtaining multiple grab samples of an environmental media to more time-integrated sampling methods (i.e., sampling that occurs over a period of days, weeks, or months to provide an average concentration). Instead of collecting a direct sample of the environmental media (e.g., water or air), time-averaged sampling involves extraction and collection of the contaminant from the environmental media over time—thus reducing the volume of the sample needed, and extending the period of time in which a time-averaged concentration can be determined. In addition, by averaging the sampling over a longer period of time, the confounding influence of spurious data is reduced, and the actual time involved in observing the key environmental variable (such as concentrations in air, water, or sediment) is greatly increased. For example, taking two grab samples per year means that just two brief moments in time represent the entire year of concentrations in the environment. A three-month integrative sampling, however, can increase this temporal coverage. Also, the costs for performing time-integrated sampling in environmental media can be significantly less compared to conventional grab sampling methods because repetitive field trips to do the sampling are not needed.

Various examples of time-integrated samplers are available to measure concentrations of volatile organic compounds (VOCs). For instance, the 24-hr Summa canisters or 7-day passive sorbent samplers have been the default devices for measuring VOC concentrations in air. Various samplers that measure average concentrations of semi-volatiles in sediments over multi-month periods are also available. In groundwater, deployment periods for currently-available time-integrated samplers are constrained by the design of those samplers, where current groundwater samplers (e.g., AGI Universal Sampler aka Gore Sorber, Enviroflux, etc.) are typically deployed over a time period of only hours to 28 days, such as disclosed in U.S. Pat. No. 6,401,547 to Enviroflux.

Each of these devices is a form of "kinetic" sampler, where the sampler is designed to have a constant uptake rate throughout the sampling duration. Unfortunately, kinetic samplers can face limitations that compromise the accuracy of the measurements over an extended time period. Specifically, kinetic samplers are sensitive to changes in the flow velocity of the medium (e.g., air or water), which can alter the thickness of the sampler's boundary diffusion layer (comprised of a stagnant fluid layer in front of a membrane and the membrane itself). In turn, this sensitivity can affect the concentration's gradient across the layer and ultimately can affect the contaminant's mass that is trapped within the sampler (e.g., adsorbed to a sorbent). Consequently, uptake rates can vary in kinetic samplers if changes in the ambient fluid flow velocity change the thickness of the kinetic sampler's diffusion layer.

Also, kinetic samplers are subject to potential biofouling, degradation of their membranes and/or sorbents, or other detrimental processes that change the sampler's uptake rate or otherwise cause sampling errors. Moreover, these detrimental processes can limit the effective deployment time of the sampling device in certain settings.

For at least these reasons, a time-integrated sampler is needed that addresses these limitations and provides a dependable and effective method for the measurement of average constituent concentrations in a fluid over an extended period of time (i.e., months). Such a time-integrated sampler could potentially eliminate most short-term variability problems that now plague monitoring programs based on the individual grab samples. To that end, the subject matter of the present disclosure is directed to overcoming, or at least reducing the effects of, one or more of the problems set forth above.

SUMMARY OF THE DISCLOSURE

A system, device, and method are disclosed for quantitatively measuring average concentrations of target constituents (e.g., volatile organic compounds (VOCs)) in an ambient fluid (e.g., groundwater, surface water, air, etc.) over an extended period of time. The system uses a passive device having an outer equilibration chamber and an inner kinetic sampler. The device is placed in an ambient fluid for a specified period of time, wherein the target constituent(s) rapidly diffuse through a high-permeability membrane into the fluid-filled equilibration chamber. From there, the target constituents are taken up by the kinetic sampler.

In a first embodiment, a passive sampling device is used for measuring an average concentration of one or more target constituents in an ambient fluid (e.g., water, air) over a deployment period. The device comprises an equilibration chamber and at least one kinetic sampler. The equilibration chamber has a first inlet, and a first membrane of a first permeability is disposed at the first inlet. The first membrane defines an equilibration rate and controls the equilibration of the one or more target constituents between the ambient fluid and the equilibration chamber.

The at least one kinetic sampler is in fluid communication with the equilibration chamber. For example, the at least one kinetic sampler can be disposed inside the chamber. Each of the at least one kinetic samplers has an uptake rate for the one or more target constituents. The uptake rate is configured to be less than the equilibration rate of the first membrane and is configured to maintain the equilibration between the equilibration chamber and the ambient fluid.

The equilibration chamber can have an initial fluid contained therein, such as air, water, or an organic fluid. Also, the at least one kinetic sampler can be a sorbent sampler disposed inside the equilibration chamber. The at least one kinetic sampler can include more than one kinetic sampler disposed inside the equilibration chamber to increase a detection range of the one or more target constituents and/or to increases a measurement range of the concentrations and/or to increase the variety of target constituents.

The at least one kinetic sampler can include a second membrane defining at least in part the uptake rate for the one or more target constituents. For example, the second membrane may have a second permeability and can be disposed at a second inlet of the at least one kinetic sampler. The second permeability defines at least in part the uptake rate for the one or more target constituents of the at least one kinetic sample. Also, the second permeability is configured to be less than the first permeability of the first membrane.

The at least one kinetic sampler can have an engineered feature or geometric structure that at least in part defines the uptake rate for the one or more target constituents. For example, the at least one kinetic sampler can have a sorbent tube with an area and a length that defines at least in part the uptake rate.

Inside the equilibration chamber, for example, target constituent(s) in the equilibration chamber diffuse through the second membrane of the inner kinetic sampler at an uptake rate proportional to their given concentration in the equilibration chamber. The uptake rate is configured to (a) not significantly disturb the equilibrium of target constituents between the ambient fluid and the equilibration chamber, (b) attain suitable detection limits, and (c) avoid saturation of a sample medium or a sorbent within the at least one kinetic sampler. At the end of the sample period, the resultant mass of the target constituent(s) within the kinetic sampler can be used to determine the average concentration of target constituent(s) over time in the ambient fluid based on the known uptake rate of the kinetic sampler for the target constituent(s) and the known partitioning between the ambient fluid and the fluid in the equilibration chamber.

Stated another way, the kinetic sampler disposed inside the equilibration chamber has an uptake rate that is slow relative to the rate of equilibration between the equilibration chamber and the ambient fluid so that the kinetic sampler does not significantly disturb the equilibrium between the equilibration chamber and the external ambient fluid. In addition, the uptake rate for the kinetic sampler is set suitably high to obtain desired detection limits for the target constituent(s) and suitably low to avoid saturation of the sampling medium or sorbent in the kinetic sampler.

The use of the outer equilibration chamber with the high permeability membrane can eliminate the effects of variable flow velocity of the ambient fluid on the uptake rate of the at least one kinetic sampler. This two-stage arrangement also protects the kinetic sampler from biofouling and other weathering processes that can change its uptake rate. In this way, changes in permeability of the outer membrane on the outer equilibration chamber due to biofouling or other weathering processes will not adversely affect the contaminant uptake rate of the inner kinetic sampler, as long as the permeability of the equilibration chamber's membrane remains significantly high (so that the uptake of target constituent(s) by the kinetic sampler does not significantly disturb the equilibrium between the equilibration chamber and the ambient fluid). In other words, the outer membrane between the equilibration chamber and the ambient fluid is designed with "reserve capacity" so that some loss of its permeability due to weathering will not affect its ability to maintain equilibrium with the ambient fluid.

Inside the equilibration chamber, the kinetic sampler is designed to capture the target constituent(s) at a rate proportional to their concentration in the equilibration chamber (i.e., the kinetic sampler has a constant uptake rate). For example, the kinetic sampler may contain a sorbent material separated from the equilibration chamber by a second, low-permeability membrane. The second membrane on the kinetic sampler is configured so the known uptake rate can be exploited, in combination with (a) the mass of each compound trapped within the sampler and (b) the exposure time of the sampler, to determine the average concentration of the target constituent(s) in the ambient fluid over a specified time.

The time-integrated sampling device of the present disclosure may be deployed with an extended deployment time (e.g., three months or more), which can dramatically reduce issues with short-term variability in the concentrations. As noted herein, the disclosed device can then avoid problems of biofouling by using the vapor-phase sorb ent and two separate diffusion membranes: the first, high-permeability membrane at the interface with the ambient fluid and the second, low-permeability membrane at the sorbent interface of the inner sampler. This configuration prevents bacterial degradation of the sorbent in the kinetic sampler by keeping the sorbent isolated from the environment. Biofouling of the high-permeable membrane will not appreciably affect the contaminant uptake rate as long as the permeability of this membrane remains higher than that of the inner low-permeable membrane. The potential for longer-term degradation of the sorbed contaminant during deployment is also minimized by separating the sorbent from the ambient fluid.

According to one embodiment, a passive sampling method involves deploying a sampling device in an ambient fluid. One or more target constituents in the ambient fluid diffuse at an equilibration rate through a first membrane of an equilibration chamber on the sampling device. One or more target constituents in the equilibration chamber diffuse at an uptake rate into at least one kinetic sampler in fluid communication with the equilibration chamber.

Disturbance of the equilibrium between the equilibration chamber and the ambient fluid is minimized based on the uptake rate of the at least one kinetic sampler being less than the equilibration rate of the first membrane. The method involves measuring from the at least one kinetic sampler one or more concentrations of the one or more target constituents in the ambient fluid over a deployment period.

For example, the disclosed sampling device can be deployed in a monitoring well or other environment for an extended deployment period, such as a 90-day time period. The target constituents rapidly equilibrate between the ambient fluid and the device's equilibration chamber. Uptake of the target constituents onto a sorbent in the kinetic sampler can thereby be proportional to the concentration of target constituents in the equilibration chamber. As a result, the mass of target constituents on the sorbent and the deployment time can be used to determine the time-weighted average target constituent's concentration in ambient fluid over the deployment period.

A mathematical model can be used to select the permeability of the first membrane, to select the uptake rate for the kinetic sampler, and/or to configure other characteristics, such as the volume of the equilibration chamber to meet the needs of a particular implementation.

According to one embodiment, a method of assembling a passive sampling device for measuring one or more concentrations of one or more target constituents in an ambient fluid over a deployment period involves configuring an equilibration rate for an equilibration chamber of the sampling device by selecting a first membrane of a first permeability for an inlet of the equilibration chamber. An uptake rate for the one or more target constituents into at least one kinetic sampler of the sampling device is configured to be less than the equilibration rate of the first membrane. The at least one kinetic sampler is placed in fluid communication with the equilibration chamber.

For assembly, for example, the selected at least one kinetic sampler is placed inside the equilibration chamber, and the equilibration chamber is filled with an initial fluid (e.g., air, water, or organic liquid), which is free of the target constituents but is capable of transmitting the target constituents between the chamber's first membrane and the kinetic sampler. Next, the inlet of the equilibration chamber is covered with the first membrane selected such that the equilibration rate for the target constituents between the ambient fluid and the equilibration chamber is higher than the kinetic uptake rate for the selected kinetic sampler. With this first membrane secured in place with a fastener, the assembled sampling device is ready for deployment in the ambient fluid being sampled. The assembled sampling device is deployed in the ambient fluid for a defined sample period (e.g., three months) and then retrieved. Finally, the kinetic sampler is recovered from the sampling device for analysis.

According to one embodiment, a method is used for determining one or more concentrations of one or more target constituents in an ambient fluid. The method involves the following steps: (1) deploying the disclosed sampling device in the ambient fluid for a defined period of time, (2) recovering the sampling device from the ambient fluid and removing of the kinetic sampler, (3) extracting the target constituents from the kinetic sampler (typically completed using thermal or solvent extraction), (4) measuring the mass of recovered target constituents using an appropriate measurement instrument (for example, a gas chromatograph for measurement of VOCs), and (5) calculating the average concentration of the target constituents in the ambient fluid based on the measured mass of target constituents, the sampler deployment time, and the known sampling characteristics of the sampler (e.g., the uptake rate of the kinetic sampler).

The foregoing summary is not intended to summarize each potential embodiment or every aspect of the present disclosure.

DETAILED DESCRIPTION OF THE DISCLOSURE

Figures 1A, 1B:
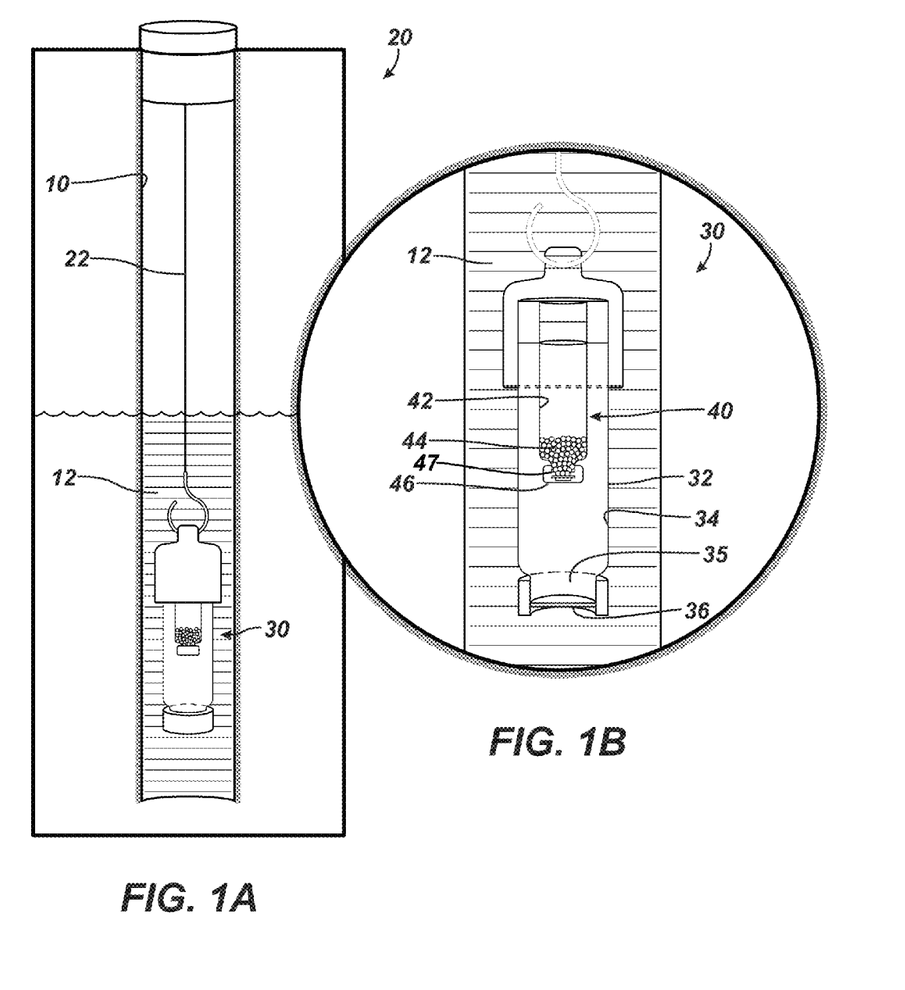
FIG. 1A illustrates a time-integrated sampling system according to the present disclosure used in an environmental medium, such as groundwater in a well.
FIG. 1B illustrates a detail of a sampling device for the system in FIG. 1A.

FIG. 1A shows an embodiment of a time-integrated sampling system 20 according to the present disclosure. The disclosed system 20 can be used for measuring an average concentration of one or more target constituents (e.g., volatile organic compound (VOC) concentrations) in an ambient fluid (e.g., air, groundwater, or other source) over a deployment period. The system 20 includes a sampling device 30 that suspends in the ambient fluid to perform the time-integrated sampling. For example, the device 30 can be suspended by a tether 22 or the like in groundwater 12 of a well 10.

As shown in the detail of FIG. 1B, the sampling device 30 includes an outer container 32, a first permeable membrane 36, and a kinetic sampler 40. The outer container 32 defines an equilibration chamber 34 having a first inlet 35. The first membrane 36 is disposed across the first inlet 35 and separates the chamber 34 from the ambient fluid 12. The kinetic sampler 40 is disposed in fluid communication with the equilibration chamber 34. As shown here, the kinetic sampler 40 is disposed inside the equilibration chamber 34, which holds one kinetic sampler 40 (although more than one can be used as discussed later).

The first membrane 36 disposed at the chamber's inlet 35 has a first permeability. When the device 30 is disposed in the ambient fluid 12, the first membrane 36 allows equilibration at an equilibration or first uptake rate of the one or more target constituents between the ambient fluid 12 and the equilibration chamber 34. For example, the first membrane 36 can have a high permeability between the ambient fluid 12 and the equilibration chamber 34, which contains an initial fluid, such as air. In this way, the high-permeability membrane 36 allows for rapid equilibration between ambient fluid 12 (e.g., groundwater in the monitoring well) and the initial fluid (e.g., air) in the chamber 34. This equilibration may take less than about seven days or so.

Inside the chamber 34, the kinetic sampler 40 has a second uptake rate for the one or more target constituents. In particular, the sampler's uptake rate is less than the equilibration rate of the first membrane 36 so the sampler's uptake rate can minimize a disturbance of the equilibrium between the equilibration chamber 34 and the surrounding ambient fluid 12.

As disclosed herein, several types of kinetic samplers 40 can be used in the sampling device 30. In one embodiment, the kinetic sampler 40 has a membrane defining at least in part the sampler's uptake rate for the one or more target constituents, and the sampler 40 can contain a sorbent. In other embodiments, the kinetic sampler 40 can have one or more engineered features or geometric structures that at least in part define the sampler's uptake rate for the one or more target constituents. For example, the kinetic sampler 40 can be a sorbent tube having an area and a length configured to provide the desired uptake rate. As will be appreciated by one skilled in the art having the benefit of the present disclosure, the disclosed device 30 can use these and other types of kinetic samplers 40.

Figure 2A:
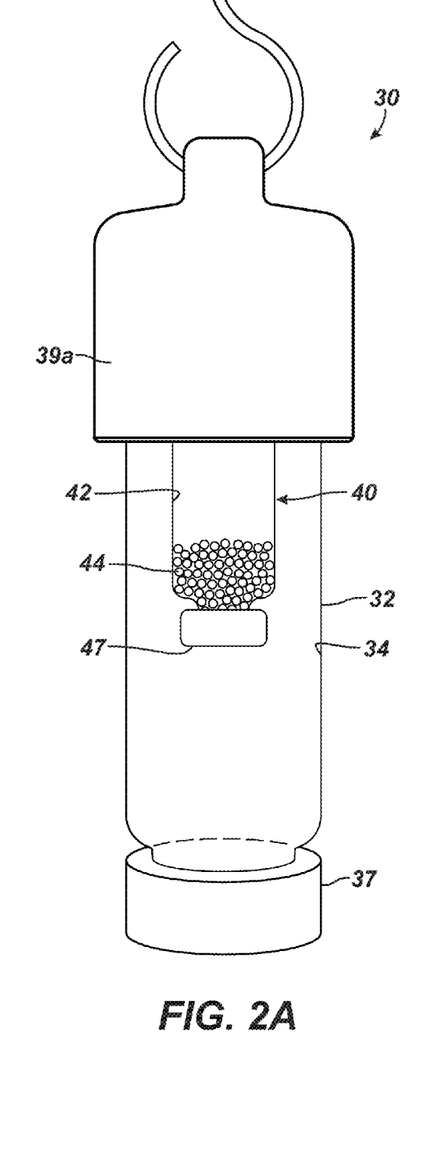
FIGS. 2A-2B illustrate elevational and cross-sectional views of a sampling device of the present disclosure.
Figure 2B:
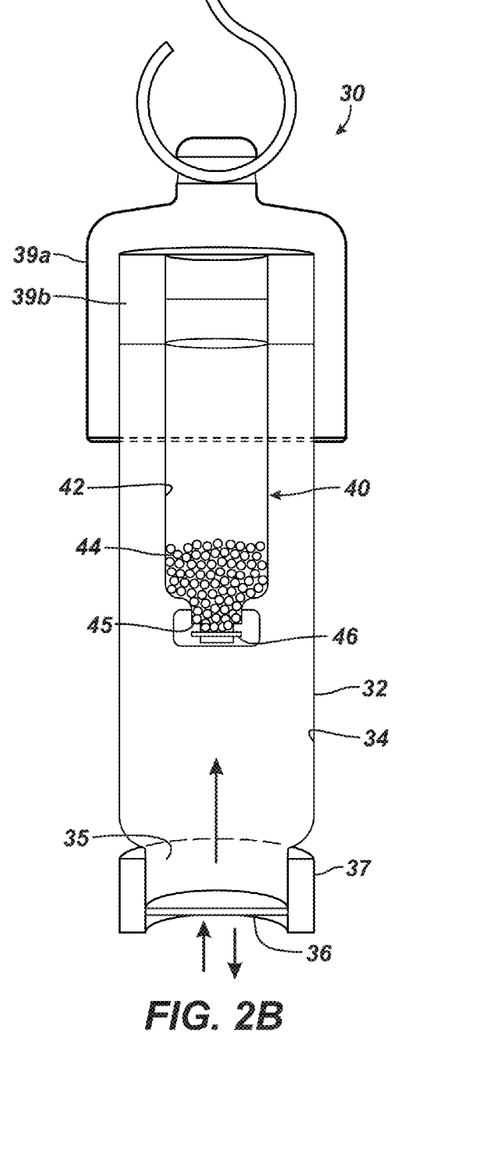

FIGS. 2A-2B show particular details of a sampling device 30 according to one embodiment. The container 32 housing the outer equilibration chamber 34 can be composed of glass, plastic, or metal. The inlet 35 for the chamber 34 can be an opening at the base of the container 32 covered with the first permeable membrane 36, which can be held by a grommet or other fastener 37 on the container 32. For its part, the first permeable membrane 36 can be a low-density polyethylene membrane.

The kinetic sampler 40 can be affixed inside the chamber 34 in a number of ways. For example, a gasket 39b composed of Teflon or nylon can affix and seal the sampler 40 inside the top of the container 32, and a top cover or cap 39a can affix to the top of the container 32 for connection to a tether or the like.

The kinetic sampler 40 itself includes a container 42 that can be composed of glass, plastic, or metal. The container 42 can hold a sorbent 44 therein. Such a sorbent 44 is used to "trap" the target constituent(s) within the kinetic sampler 40. In general, the kinetic sampler 40 can be similar to sorbent tubes, a "Waterloo Membrane Sampler," or a "SKC VOC Chek."

In this embodiment, the kinetic sampler 40 uses a membrane, which at least in part defines the sampler's uptake rate. In particular, the inlet 45 of the sampler 40 can be an opening in the sampler's container 42 covered by a second permeable membrane 46, which can be held by a fixture 47 on the base of the container 42. As will be discussed later, the second membrane 46 has a second permeability that is less than the first permeability of the first membrane 36.

As hinted to above, the outer container 32 is initially filled with a fluid, such as air, water, or an organic fluid, containing no detectable concentrations of the target constituent(s). When the device 30 is disposed in the ambient fluid (12) to be measured, the target constituents diffuse through the first membrane 36 into the equilibration chamber 34. Overtime, the kinetic sampler 40 then collects the one or more target constituents diffusing through the second membrane 46 (or other engineered feature), and any sorbent 44 in the sampler's container 42 can absorb the target constituents.

As configured, the second membrane 46 of low permeability controls the kinetic uptake for the one or more target constituents between the equilibration chamber 34 and sampler's container 42 and the sorbent 44 inside the sampler 40. The second membrane 46 preferably allows for constant uptake of contaminants (at a rate proportional to concentration in the equilibration chamber 34) without disturbing the equilibrium with the ambient fluid (12). As a result, the uptake rate of the VOC constituent's mass on to the sorbent 44 is proportional to the VOC concentration in the ambient fluid (12). The time-averaged VOC concentration in the ambient fluid (12) is thereby calculated based on (i) the mass of the VOC measured on the sorbent 44, (ii) the uptake rate for the sorbent sampler 40, (iii) Henry's law constant for partitioning between the subject fluids (e.g., water and air), and (iv) the total deployment time (e.g., 90 days).

As noted above, the second membrane 46 has a sufficiently low uptake rate to avoid significant disturbance of the equilibrium between the equilibration chamber 34 and the ambient fluid (12). However, the uptake rate is sufficiently high to attain acceptable detection limits of the target constituent(s) over a planned deployment period. Additionally, because the sorbent 44 may be used in the sampler 40, the second membrane 46 preferably has an uptake rate sufficiently low to avoid saturation of the sorbent 44 over the planned deployment period.

Materials for the first and second membranes 36, 46 on the equilibration chamber 34 and kinetic sampler 40 are selected based on a number of considerations. The two membranes 36, 46 are configured to produce rapid equilibration between the external ambient fluid (e.g., groundwater) and the initial fluid (e.g., air) in the equilibration chamber 34. Additionally, the two membranes 36, 46 are configured so that the uptake rate of target constituent(s) into the kinetic sampler 40 is slow relative to the equilibration rate in the outer chamber 34. This is done so that the slow uptake into the kinetic sampler 40 has negligible impact on the equilibrium.

The particular materials, thickness, area, and the like for the membranes 36, 46 and the sorbent 44 are selected in part based on the ambient fluid (12) to be sampled, the target constituent(s) to be collected, and other factors. A mathematical relationship or model can be used to select the permeability of the first high-permeability membrane 36, the second low-permeability membrane 46, and/or the uptake rate for the kinetic sampler 40. As one skilled in the art will appreciate, the mathematical relationship depends on a number of factors and characteristics, such as the type of ambient fluid, the target constituents to be measured, the sorbent 44 of the sampler 40, the volume of the equilibration chamber 34, the desired deployment period, etc., which can be configured for a particular implementation.

With these considerations in mind, discussion now turns to some mathematical relationships for the components of the disclosed sampling device 30. An equilibration or uptake rate of the target constituents from the ambient fluid into the equilibrium chamber 34 of the device 30 is a function of several factors including: i) permeability of the equilibrium membrane 36, ii) the concentration of the target constituent in the ambient fluid, and iii) difference in concentration of the target constituent between the ambient fluid and the equilibration chamber 34. Thus, the equilibration or first uptake rate for the chamber 34 can be characterized by the following equation:

$$UR_{Eq} = P_{Eq} \times \frac{A_{Eq}}{T_{Eq}} \times C_A \times \frac{C_A - C_{Eq}}{C_A} \qquad \text{(Equation 1)}$$

where:
  $UR_{Eq}$=The uptake rate (g/day) from the ambient fluid into the equilibration chamber 34,
  $P_{Eq}$=Permeability (g mm/m$^2$ day) of the equilibrium membrane 36,
  $A_{Eq}$=Area (m$^2$) of the equilibrium membrane 36,
  $T_{Eq}$=Thickness (mm) of the equilibrium membrane 36,
  $C_A$=The concentration (mol/mol) of the target constituent in the ambient fluid, and
  $C_{Eq}$=The concentration (mol/mol) of the target constituent in the equilibration chamber 34.

For this first Equation (1), the concentration of the target constituent in the ambient fluid and the equilibration chamber 34 should be expressed using the same units of measure. If the fluid in the equilibration chamber 34 is different from the ambient fluid, then a conversion may be needed. For example, Henry's Law can be used to express a water concentration as an equivalent gas-phase concentration.

In contrast to the above equilibration or uptake rate for the equilibration chamber 34, a second uptake rate of the target analyte(s) into the kinetic sampler 40 is independent of the mass (or concentration) of the target constituent(s) in the kinetic sampler 40 because the sorbent 44 used in the kinetic sampler 40 results in an effective concentration inside the kinetic sampler 40 of zero. Thus, the uptake rate for the kinetic sampler 40 can be characterized as follows:

$$UR_{KS} = P_{KS} \times \frac{A_{KS}}{T_{KS}} \times C_{Eq} \qquad \text{(Equation 2)}$$

where:
- $UR_{KS}$=The uptake rate (g/day) from the equilibration chamber 34 into the kinetic sampler 40,
- $A_{Ks}$=Permeability (g mm/m² day) of the kinetic sampler membrane 46,
- $A_{Ks}$=Area (m²) of the kinetic sampler membrane 46,
- $T_{Ks}$=Thickness (mm) of the kinetic sampler membrane 46, and
- $C_{Eq}$=The concentration (mol/mol) of the target constituent in the equilibration chamber 34.

After an initial equilibration period, the sampler 40 will achieve a steady state condition such that the first uptake of the target constituent from the ambient fluid into the equilibration chamber 34 will be equal to the uptake rate from the equilibrium chamber into the kinetic sampler 40. Under this steady-state condition, the difference in the concentration of the target constituent between the ambient fluid and the equilibration chamber 34 can be calculated using Equations 1 and 2 based on the known permeability, area, and thickness of the equilibration chamber membrane 36 and kinetic sampler membrane 46.

If the initial equilibration period is short relative to the total deployment time of the sampling device 30 and the difference in the concentration of the target constituent between the ambient fluid and the equilibration chamber 34 is small, then the concentration of the target analyte in the ambient fluid can be approximated as:

$$C_A = \frac{1}{P_{KS}} \times \frac{T_{KS}}{A_{KS}} \times \frac{M_{KS}}{DT} \qquad \text{(Equation 3)}$$

where:
- $C_A$=The concentration (mol/mol) of the target constituent in the ambient fluid,
- $P_{Ks}$=Permeability (g mm/m² day) of the kinetic sampler membrane 46,
- $A_{Ks}$=Area (m²) of the kinetic sampler membrane 46,
- $T_{Ks}$=Thickness (mm) of the kinetic sampler membrane 46,
- $M_{KS}$=Mass (g) of target analyte measured on the kinetic sampler 46 at the end of the deployment period, and
- $D_T$=The deployment time (days) of the sampling device 30.

If the initial equilibration period is not short relative to the total deployment time of the sampling device 30 or the difference in the concentration of the target constituent between the ambient fluid and the equilibration chamber 34 is small, then the concentration of the target analyte in the ambient fluid can more accurately be determined using a simple numerical model that accounts for both the equilibration period and the difference in the concentration of the target constituent between the ambient fluid and the equilibration chamber 34.

As will be recognized, the above equations are exemplary. Additionally, the above equations are directed to the embodiment of the disclosed kinetic sampler 40 that uses the membrane 46. Parameters of the equations can be readily modified for other types of kinetic samplers as disclosed herein lacking a membrane, such as a sorbent tube with an uptake rate defined by area and length.

Before use, the sampling device 30 can be stored in a protective container that prevents any potential uptake of target constituent(s) during shipment. Upon opening the protective container at a site, the sampling device 30 is active. During use as noted in FIG. 1, the device 30 may be hooked on to a tether 22, such as a stainless steel wire or other suspension device, and can be deployed in a sampling environment, such as a monitoring well 10.

The sampling device 30 then collects its time-integrated sample over a deployment period. At the end of the deployment period, the sampling device 30 is retrieved from the sampling environment using the tether 22. At this point, the equilibration chamber 34 is opened, for example, by removing the top gasket 39 from the container 32. The kinetic sampler 40 is removed and placed inside a protective container to prevent further uptake of the target constituent(s) during shipment to a laboratory for appropriate analysis. In the end, the device 30 can be disposable.

For analysis, the sampling device 30 acts as a passive diffusion sampler filled with an initial fluid (e.g., air or the like). VOC constituents diffuse into the sampling device 30, and diffuse into the kinetic sampler 40, where they are sorbed to a sorbent 44. Acting as a passive sorbent vapor sampler, the kinetic sampler 40 is configured so the known uptake rate can be exploited to determine the average concentration of VOC constituents in the vapor phase. If the equilibration chamber 34 contains a different fluid than the ambient fluid (e.g., air vs. water), then the corresponding VOC concentration in the ambient fluid can be determined by applying a Henry's Law calculation, giving final results in ug/L or mg/L. In this way, the sampling device 30 quantitatively measures concentrations of target constituents in the ambient fluid as a passive sampler placed in the environmental medium (e.g., groundwater, surface water, air, etc.) for an extended period of time.

The sampling device 30 solves a number of limitations associated with currently available samplers. First, the sampling device 30 reduces the effects of variable flow velocities of ambient fluid on uptake rates of the kinetic sampler 40. Second, the sampling device 30 reduces the effects of detrimental processes, such as weathering, biofouling, or degradation of the sampler's membrane 46 or sorbent 44, that can hinder the uptake rates of the kinetic sampler 40.

These two limitations are addressed by separating the kinetic sampler 40 from the ambient fluid (12) with the fluid-filled equilibration chamber 34. The highly permeable first membrane 36 serves as the interface between the outer equilibration chamber 34 and the ambient fluid being sampled. This first membrane 36 facilitates rapid equilibration of target constituent(s) concentrations between the ambient fluid and equilibration chamber 34. In some instances, the equilibration chamber 34 may attain about 90% of concentrations at equilibrium with the ambient fluid within about 10% or less of the device's deployment time.

Figure 3A:
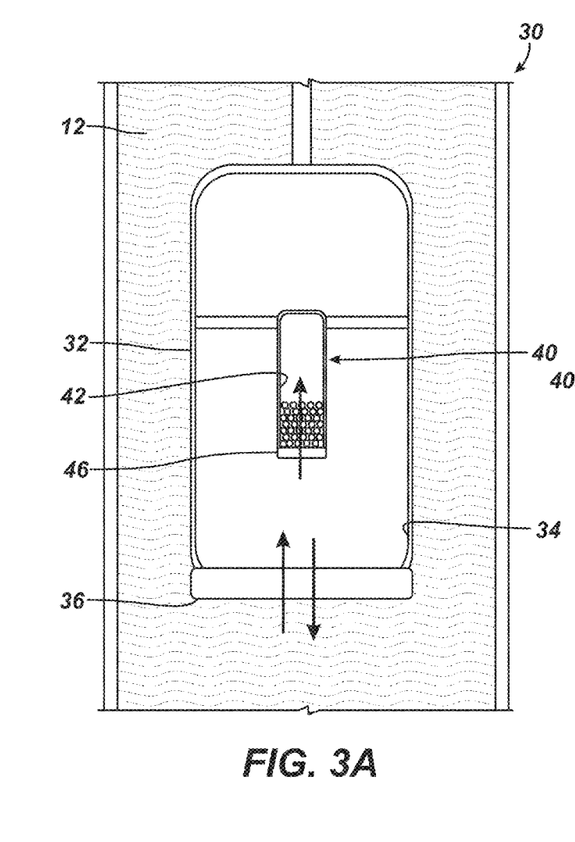
FIGS. 3A-3B illustrate schematic views of the disclosed sampling device respectively having one and more than one kinetic sampler.
Figure 3B:
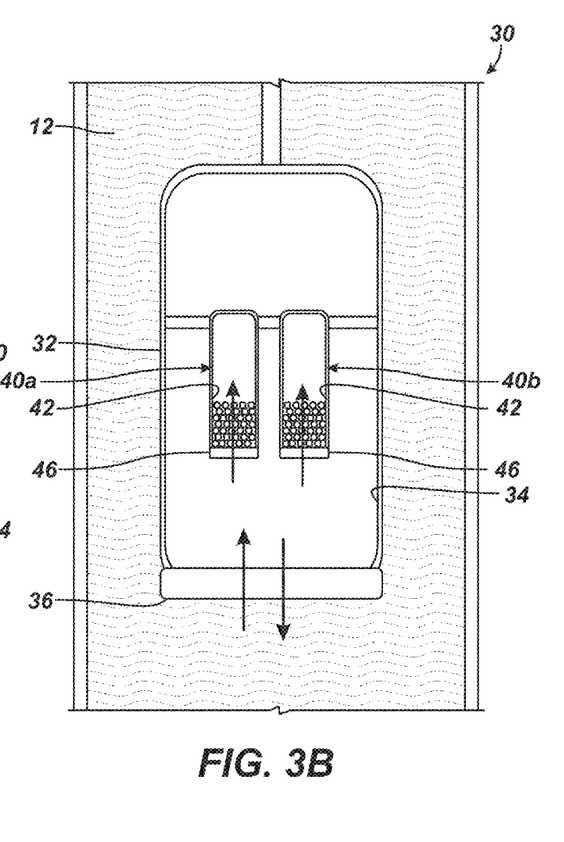
Figure 4:
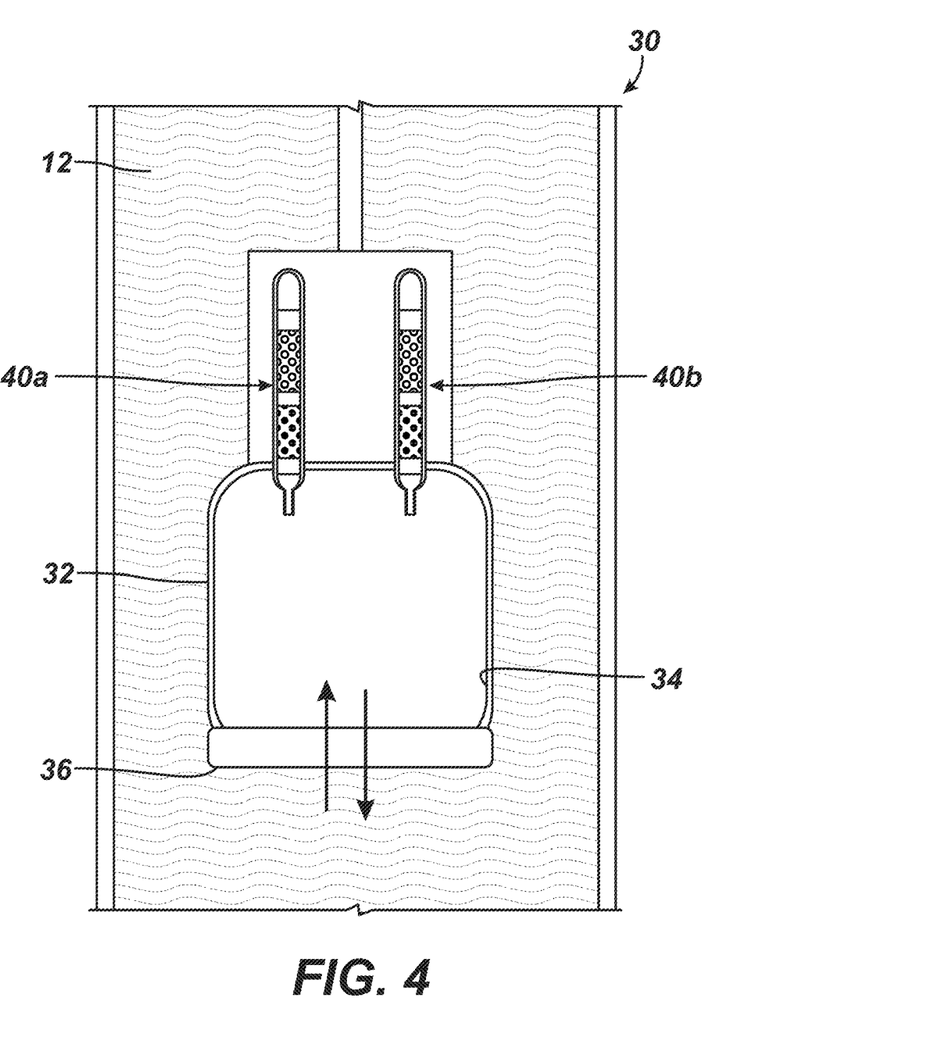
FIG. 4 illustrates a schematic view of the disclosed sampling device having more than one sorb ent tubes in fluid communication with an equilibration chamber.

As noted briefly above, one or more kinetic samplers 40 can be placed in fluid communication or disposed inside the equilibration container 32. FIG. 3A shows a schematic representation of the disclosed sampling device 30 with one kinetic sampler 40 disposed in the container 32. By way of another example, FIG. 3B shows a schematic representation of the disclosed device 30 with two kinetic samplers 40a-b disposed in the container 32 to provide additional sampling benefits. Furthermore, FIG. 4 illustrates a schematic view of the disclosed sampling device 30 having sorbent tubes 40a-b in fluid communication with the equilibration chamber 34. (Like reference numbers are used for similar components between Figures.)

As can be seen, multiple kinetic samplers 40a-b can disposed inside the equilibration chamber 34. In the end, the multiple samplers 40a-b can increase a detection range of the one or more target constituents, increase a measurement range of the concentrations, increase the variety of target constituents, and/or provide a level of redundant sampling. All the same, the uptake rates of the multiple samplers 40a-b are still less than the equilibration rate.

The foregoing description of preferred and other embodiments is not intended to limit or restrict the scope or applicability of the inventive concepts conceived of by the Applicants. It will be appreciated with the benefit of the present disclosure that features described above in accordance with any embodiment or aspect of the disclosed subject matter can be utilized, either alone or in combination, with any other described feature, in any other embodiment or aspect of the disclosed subject matter.

In exchange for disclosing the inventive concepts contained herein, the Applicants desire all patent rights afforded by the appended claims. Therefore, it is intended that the appended claims include all modifications and alterations to the full extent that they come within the scope of the following claims or the equivalents thereof.

What is claimed is:

1. A passive sampling device for measuring one or more concentrations of one or more target constituents in an ambient fluid over a deployment period, the device comprising: an equilibration chamber having a first inlet; a first membrane of a first permeability disposed at the first inlet and defining an equilibration rate, the equilibration rate controlling equilibration of the one or more target constituents between the ambient fluid and the equilibration chamber; and at least one kinetic sampler in fluid communication with the equilibration chamber, each of the at least one kinetic samplers having an uptake rate for the one or more target constituents, the uptake rate being less than the equilibration rate of the first membrane and maintaining the equilibration between the equilibration chamber and the ambient fluid.

2. The device of claim 1, wherein the at least one kinetic sampler comprises a sorbent sampler disposed inside the equilibration chamber.

3. The device of claim 1, wherein the at least one kinetic sampler comprises more than one of the at least one kinetic sampler increasing a detection range of the one or more target constituents and/or increasing a variety of the target constituents.

4. The device of claim 1, wherein the at least one kinetic sampler comprises more than one of the at least one kinetic sampler increasing a measurement range of the one or more concentrations.

5. The device of claim 1, wherein the uptake rate of the at least one kinetic sampler is configured to at least one of: (a) maintain the equilibration of the one or more target constituents between the ambient fluid and the equilibration chamber, (b) attain a detection limit of the one or more target constituents in the at least one kinetic sampler, and (c) prevent saturation of a sample medium or a sorbent within the at least one kinetic sampler.

6. The device of claim 1, wherein the at least one kinetic sampler contains a resultant mass of the one or more target constituents indicative of an average of the one or more concentrations of the one or more target constituents in the ambient fluid during the deployment period.

7. The device of claim 1, wherein the equilibration chamber comprises an initial fluid contained therein.

8. The device of claim 7, wherein the initial fluid contained in the equilibration chamber comprises air, water, or an organic fluid.

9. The device of claim 1, wherein the at least one kinetic sampler comprises a geometric structure defining at least in part the uptake rate for the one or more target constituents.

10. The device of claim 9, wherein the geometric structure of the at least one kinetic sampler comprises a sorbent tube having an area and a length defining at least in part the uptake rate.

11. The device of claim 1, wherein the at least one kinetic sampler comprises a second membrane defining at least in part the uptake rate for the one or more target constituents.

12. The device of claim 11, wherein the second membrane has a second permeability and is disposed at a second inlet of the at least one kinetic sampler, the second permeability being less than the first permeability of the first membrane and defining at least in part the uptake rate for the one or more target constituents.

13. The device of claim 11, wherein the second membrane is configured to diffuse the one or more target constituents therethrough at a rate proportional to a given concentration of the one or more target constituents in the equilibration chamber.

14. A method of determining one or more concentrations of one or more target constituents in an ambient fluid, comprising:
deploying the passive sampling device of claim 1 in the ambient fluid for a defined deployment period,
the passive sampling device having known sampling characteristics;
recovering the passive sampling device from the ambient fluid;
removing the kinetic sampler from the sampling device for analysis;
extracting the target constituents from the kinetic sampler;
measuring mass of the recovered target constituents; and
calculating an average concentration of the target constituents in the ambient fluid based on the mass of the recovered target constituents, the defined deployment period, and the known sampling characteristics of the sampling device.

15. A passive sampling method, comprising: deploying a sampling device in an ambient fluid; diffusing one or more target constituents in the ambient fluid at an equilibration rate through a first membrane of an equilibration chamber on the sampling device; diffusing one or more target constituents in the equilibration chamber at an uptake rate into at least one kinetic sampler in fluid communication with the equilibration chamber; minimizing disturbance of the equilibrium between the equilibration chamber and the ambient fluid based on the uptake rate of the at least one kinetic sampler being less than the equilibration rate of the first membrane; and measuring from the at least one kinetic sampler one or more concentrations of the one or more target constituents in the ambient fluid over a deployment period.

16. The method of claim 15, wherein the at least one kinetic sampler comprises a sorbent sampler.

17. The method of claim 15, wherein diffusing the one or more target constituents in the equilibration chamber at the uptake rate into at least one kinetic sampler comprises increasing a detection range of the one or more target constituents by using more than one of the at least one kinetic sampler in fluid communication with the equilibration chamber.

18. The method of claim 15, wherein diffusing the one or more target constituents in the equilibration chamber at the uptake rate into at least one kinetic sampler comprises increasing a measurement range of the one or more concentrations by using more than one of the at least one kinetic sampler in fluid communication with the equilibration chamber.

19. The method of claim 15, wherein deploying the sampling device in the ambient fluid comprises deploying the equilibration chamber with an initial fluid contained therein.

20. The method of claim 15, wherein diffusing the one or more target constituents in the equilibration chamber at the uptake rate diffusing through a sorbent tube having an area and a length defining at least in part the uptake rate.

21. The method of claim 15, wherein minimizing the disturbance of the equilibrium between the equilibration chamber and the ambient fluid based on the uptake rate of the at least one kinetic sample being less than the equilibration rate of the first membrane comprises configuring the uptake rate to at least one of: (a) maintain the equilibration of the one or more target constituents between the ambient fluid and the equilibration chamber, (b) attain a detection limit of the one or more target constituents in the at least one kinetic sampler, and (c) prevent saturation of a sample medium or a sorbent within the at least one kinetic sampler.

22. The method of claim 15, wherein measuring from the at least one kinetic sampler the one or more concentrations of the one or more target constituents in the ambient fluid over the deployment period comprises determining a resultant mass of each of the one or more target constituents indicative of an average of the one or more concentrations of the one or more target constituents in the ambient fluid during the deployment period.

23. The method of claim 15, wherein diffusing the one or more target constituents in the ambient fluid at the equilibration rate through the first membrane of the equilibration chamber on the sampling device comprises one or more of: reducing an effect of variable flow velocity of the ambient fluid on the uptake rate of the at least one kinetic sampler; protecting the uptake rate of the at least one kinetic sampler from fouling; and separating a sample medium or a sorbent within the at least one kinetic sampler from the ambient fluid.

24. The method of claim 15, wherein diffusing the one or more target constituents in the equilibration chamber at the uptake rate into at least one kinetic sampler in fluid communication with the equilibration chamber comprises diffusing through a second membrane of the at least one kinetic sampler defining at least in part the uptake rate for the one or more target constituents.

25. The method of claim 24, wherein minimizing the disturbance of the equilibrium between the equilibration chamber and the ambient fluid based on the uptake rate of the at least one kinetic sampler being less than the equilibration rate of the first membrane comprises selecting the second membrane with a second permeability less than the first permeability.

26. The method of claim 24, wherein diffusing through the second membrane comprises diffusing the one or more target constituents therethrough at a rate proportional to a given concentration of the one or more target constituents in the equilibration chamber.

27. A method of assembling a passive sampling device for measuring one or more concentrations of one or more target constituents in an ambient fluid over a deployment period, the method comprising: configuring an equilibration rate for an equilibration chamber of the sampling device by selecting a first membrane of a first permeability for an inlet of the equilibration chamber; configuring an uptake rate for the one or more target constituents into at least one kinetic sampler of the sampling device to be less than the equilibration rate of the first membrane; and placing the at least one kinetic sampler in fluid communication with the equilibration chamber.

28. The method of claim 27, further comprising filling the equilibrium chamber with an initial fluid free of the target constituents but capable of transmitting the target constituents between the first membrane and the kinetic sampler.

29. The method of claim 27, wherein configuring the equilibration rate for the equilibration chamber of the sampling device comprises covering the inlet of the equilibration chamber with the selected first membrane held in place with a fastener.

* * * * *